United States Patent
Denk

(10) Patent No.: US 11,399,770 B2
(45) Date of Patent: Aug. 2, 2022

(54) RESPIRATORY TRIGGERED PARASTERNAL ELECTROMYOGRAPHIC RECORDING IN NEUROSTIMULATORS

(71) Applicant: MED-EL Elektromedizinische Geraete GmbH, Innsbruck (AT)

(72) Inventor: Christian Denk, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 521 days.

(21) Appl. No.: 16/319,891

(22) PCT Filed: Aug. 1, 2016

(86) PCT No.: PCT/US2016/044956
§ 371 (c)(1),
(2) Date: Jan. 23, 2019

(87) PCT Pub. No.: WO2018/026346
PCT Pub. Date: Feb. 8, 2018

(65) Prior Publication Data
US 2019/0231268 A1 Aug. 1, 2019

(51) Int. Cl.
*A61B 5/00* (2006.01)
*A61B 5/08* (2006.01)
(Continued)

(52) U.S. Cl.
CPC .............. *A61B 5/6847* (2013.01); *A61B 5/08* (2013.01); *A61B 5/113* (2013.01); *A61B 5/389* (2021.01);
(Continued)

(58) Field of Classification Search
CPC ........... A61B 5/08; A61B 5/296; A61B 5/389; A61B 5/6847; A61N 1/3601; A61N 1/3611
See application file for complete search history.

(56) References Cited

U.S. PATENT DOCUMENTS 5,678,535 A * 10/1997 DiMarco .............. A61N 1/3601
128/200.24
5,800,470 A * 9/1998 Stein ...................... A61B 5/316
607/20
(Continued)

OTHER PUBLICATIONS

Murphy, et al., Neural respiratory drive as a physiological biomarker to monitor change during acute exacerbations of COPD, May 19, 2011, Thorax, 66, p. 602-608 (Year: 2011).*
(Continued)

*Primary Examiner* — Daniel L Cerioni
*Assistant Examiner* — Raymond P Dulman
(74) *Attorney, Agent, or Firm* — Sunstein LLP

(57) ABSTRACT

A respiration sensor is described of a respiration implant system for an implanted patient with impaired breathing. A sensor body is made of electrically insulating material and is configured to fit between two adjacent ribs and between the pectoralis muscle and the parasternal muscle of the implanted patient, with the bottom surface adjacent to an superficial surface of the parasternal muscle and the top surface adjacent to a profound surface of the pectoralis muscle. At least one parasternal sensor electrode is located on the bottom surface of the sensor body and is configured to cooperate with the electrically insulating material of the sensor body to sense a parasternal electromyography (EMG) signal representing electrical activity of the adjacent parasternal muscle with minimal influence by electrical activity of the nearby pectoralis muscle.

11 Claims, 7 Drawing Sheets

(51) Int. Cl.
  *A61B 5/113* (2006.01)
  *A61B 5/389* (2021.01)
  *A61N 1/36* (2006.01)
  *A61B 5/11* (2006.01)
  *A61B 5/296* (2021.01)

(52) U.S. Cl.
  CPC .............. *A61B 5/4818* (2013.01); *A61B 5/11* (2013.01); *A61B 5/296* (2021.01); *A61N 1/3601* (2013.01); *A61N 1/3611* (2013.01)

(56) References Cited

U.S. PATENT DOCUMENTS

| | | | |
|---|---|---|---|
| 2005/0085866 A1 | 4/2005 | Tehrani | |
| 2006/0247729 A1 | 11/2006 | Tehrani et al. | |
| 2006/0282127 A1* | 12/2006 | Zealear | A61B 5/087 607/42 |
| 2007/0161919 A1* | 7/2007 | DiLorenzo | A61B 5/0816 600/544 |
| 2012/0197329 A1 | 8/2012 | Bardy et al. | |
| 2014/0088379 A1 | 3/2014 | Irazoqui et al. | |
| 2015/0224307 A1* | 8/2015 | Bolea | A61N 1/36196 607/42 |
| 2015/0231396 A1 | 8/2015 | Burdick et al. | |
| 2015/0283382 A1 | 10/2015 | Denk et al. | |
| 2018/0235503 A1* | 8/2018 | Derkx | A61B 5/7246 |

OTHER PUBLICATIONS

International Searching Authority—EPO, International Search Report and Written Opinion, PCT/US2016/044956; dated Sep. 30, 2016, 14 pages.

European Patent Office, Extended European Search Report, Application No. 16911756.1, dated May 21, 2019, 7 pages.

* cited by examiner

RESPIRATORY TRIGGERED PARASTERNAL ELECTROMYOGRAPHIC RECORDING IN NEUROSTIMULATORS

CROSS-REFERENCE TO RELATED APPLICATIONS

This Application is a U.S. national stage entry under 35 USC § 371 of Patent Cooperation Treaty Application PCT/US2016/044956, filed Aug. 1, 2016, which is incorporated herein by reference in its entirety.

TECHNICAL FIELD

The present invention relates to respiration implant systems such as implantable respiration pacing systems and sleep apnea treatment systems.

BACKGROUND ART

The larynx is located in the neck and is involved in breathing, producing sound (speech), and protecting the trachea from aspiration of food and water. FIG. 1A shows a coronal section view and FIG. 1B shows a transverse section view of the anatomy of a human larynx including the epiglottis 101, thyroid cartilage 102, vocal folds 103, cricothyroid muscle 104, arytenoid cartilage 105, posterior cricoarytenoid muscle (PCAM) 106, vocalis muscle 107, cricoid cartilage 108, recurrent laryngeal nerve (RLN) 109, transverse arytenoid muscle 110, oblique arytenoid muscle 111, superior laryngeal nerve 112, and hyoid bone 113.

The nerves and muscles of the larynx abduct (open) the vocal folds 103 during the inspiration phase of breathing to allow air to enter the lungs. And the nerves and muscles of the larynx adduct (close) the vocal folds 103 during the expiration phase of breathing to produce voiced sound. At rest, respiration frequency typically varies from 12 to 25 breaths per minute. So, for example, 20 breaths per minute result in a 3 second breath duration, with 1.5 sec inspiration, and 1.5 sec exhalation phase (assuming a 50/50 ratio). The breathing frequency changes depending on the physical activity.

Unilateral and bilateral injuries or ruptures of the recurrent laryngeal nerve (RLN) 109 initially result in a temporal partial paralysis of the supported muscles in the larynx (and the hypolarynx). A bilateral disruption of the RLN 109 causes a loss of the abductor function of both posterior cricoarytenoid muscles (PCAM) 106 with acute asphyxia and life-threatening conditions. This serious situation usually requires surgical treatment of the bilateral vocal cord paralysis such as cordotomy or arytenoidectomy, which subsequently restrict the voice and puts at risk the physiologic airway protection.

Another more recent treatment approach to RLN injuries uses a respiration implant that electrically stimulates (paces) the PCAM 106 during inspiration to abduct (open) the vocal folds 103. During expiration, the vocal folds 103 relax (close) to facilitate voicing. In first generation respiration implant systems, the patient can vary the pacing/respiration frequency (breaths per minute) according to his physical load (at rest, normal walking, stairs, etc.) by manually switching the stimulation frequency of the pacer device, the assumption being that the human body may adapt to the artificial externally applied respiration frequency—within some locking-range. Thus the patient and the respiration pacemaker can be described as free running oscillators at almost the same frequency, but without phase-matching (no phase-locking). Sometimes both systems will be in phase, but other times the systems will be out of phase and thus the benefit for the patient will be reduced.

More recent second generation respiration implants generate a stimulation trigger signal to synchronize the timing of stimulation of the pacemaker to the respiration cycle of the patient. The stimulation trigger signal defines a specific time point during the respiration cycle to initiate stimulation of the target neural tissue. The time point may specifically be the start or end of the inspiratory or expiratory phase of breathing, a breathing pause, or any other defined time point. To detect the desired time point, several types of respiration sensors have been investigated to generate a respiration sensing signal that varies within each breathing cycle. These include, for example, various microphones, accelerometer sensors, and pressure sensors (positioned in the pleura gap). Electromyogram (EMG) measurements also are under investigation for use in developing a stimulation trigger signal.

Besides laryngeal pacemakers for RLN injuries, there also are respiration implant neurostimulators that electrically stimulate the hypoglossal nerve that innervates the root of the tongue for treatment of sleep apnea. These sleep apnea treatment systems use a respiration sensor that is implemented to trigger on the inhaling phase of breathing, for example, using a bioimpedance measurement or a pressure sensor in the pleural gap.

U.S. patent application Ser. No. 14/677,023 (incorporated herein by reference in its entirety) describes placing an intramuscular sensor within the body of the parasternal muscle. But unfortunately, that placement location can still capture a large unwanted EMG signal that originates in the overlying pectoralis muscle. The pectoralis muscle produces much larger EMG signals those of the parasternal muscle, which are induced by movements (e.g. of the arms) rather than by breathing activities as with the parasternal muscle.

SUMMARY

Embodiments of the present invention are directed to a respiration sensor of a respiration implant system for an implanted patient with impaired breathing. A sensor body is made of electrically insulating material and is configured to fit between two adjacent ribs and between the pectoralis muscle and the parasternal muscle of the implanted patient, with the bottom surface adjacent to an superficial surface of the parasternal muscle and the top surface adjacent to a profound surface lathe pectoralis muscle. At least one parasternal sensor electrode is located on the bottom surface of the sensor body and is configured to cooperate with the electrically insulating material of the sensor body to sense a parasternal electromyography (EMG) signal representing electrical activity of the adjacent parasternal muscle with minimal influence by electrical activity of the nearby pectoralis muscle.

The sensor body may specifically be paddle shaped. The at least one parasternal sensor electrode may comprise a pair of bipolar sensing electrodes, and it may be round, square or rectangular.

The respiration sensor may further include at least one pectoralis sensor electrode that is located on the top surface of the electrode body opposite the at least one parasternal sensor electrode. The at least one pectoralis sensor electrode is configured to cooperate with the electrically insulating material of the sensor body to sense a pectoralis EMG signal representing electrical activity of the adjacent pectoralis muscle. The at least one pectoralis sensor electrode may comprise a pair of bipolar sensing electrodes, and it may be round, square or rectangular. The respiration sensor also may include one or more suture attachment points that are attached to the sensor body and configured for fixedly attaching the sensor body to adjacent tissues when the respiration sensor is implanted in the implanted patient.

Embodiments of the present invention also include a respiration implant system having a respiration sensor according to any of the foregoing. The respiration implant system may specifically be a laryngeal implant system with a stimulating electrode that delivers a respiration pacing signal to the posterior cricoarytenoid muscle in the larynx. Or the respiration implant system may be a sleep apnea treatment system with a stimulating electrode that delivers a respiration pacing signal to the hypoglossal nerve or the iSLN (internal superior laryngeal nerve).

DETAILED DESCRIPTION

Various embodiments of the present invention are directed to improved respiration implants that use a respiration sensor implanted in or adjacent to the parasternal muscle to detect respiration activity in the patient with impaired breathing. Such systems may also use a three-axis acceleration sensor and/or a gyroscope as a movement/position sensor. These sensors may be in the specific form of a small device package located inside the main implant housing or outside in a separate housing communicatively connected to the main implant housing. Such respiration implant systems include, for example, laryngeal pacemaker systems and sleep apnea treatment systems.

Figure 1A:
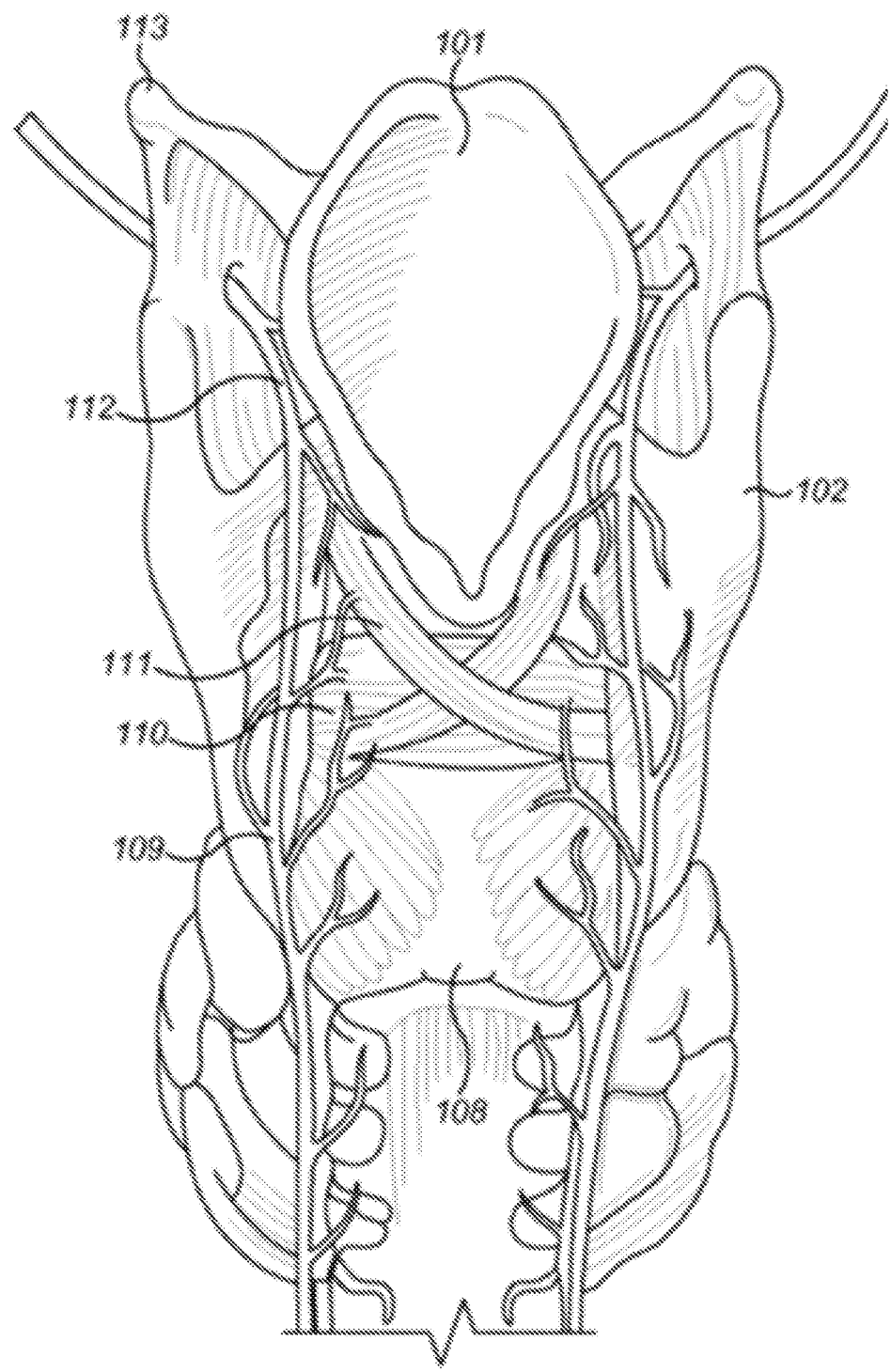
FIG. 1A shows a coronal section view and FIG. 1B shows a transverse section view of the anatomy of a human larynx.
Figure 1B:
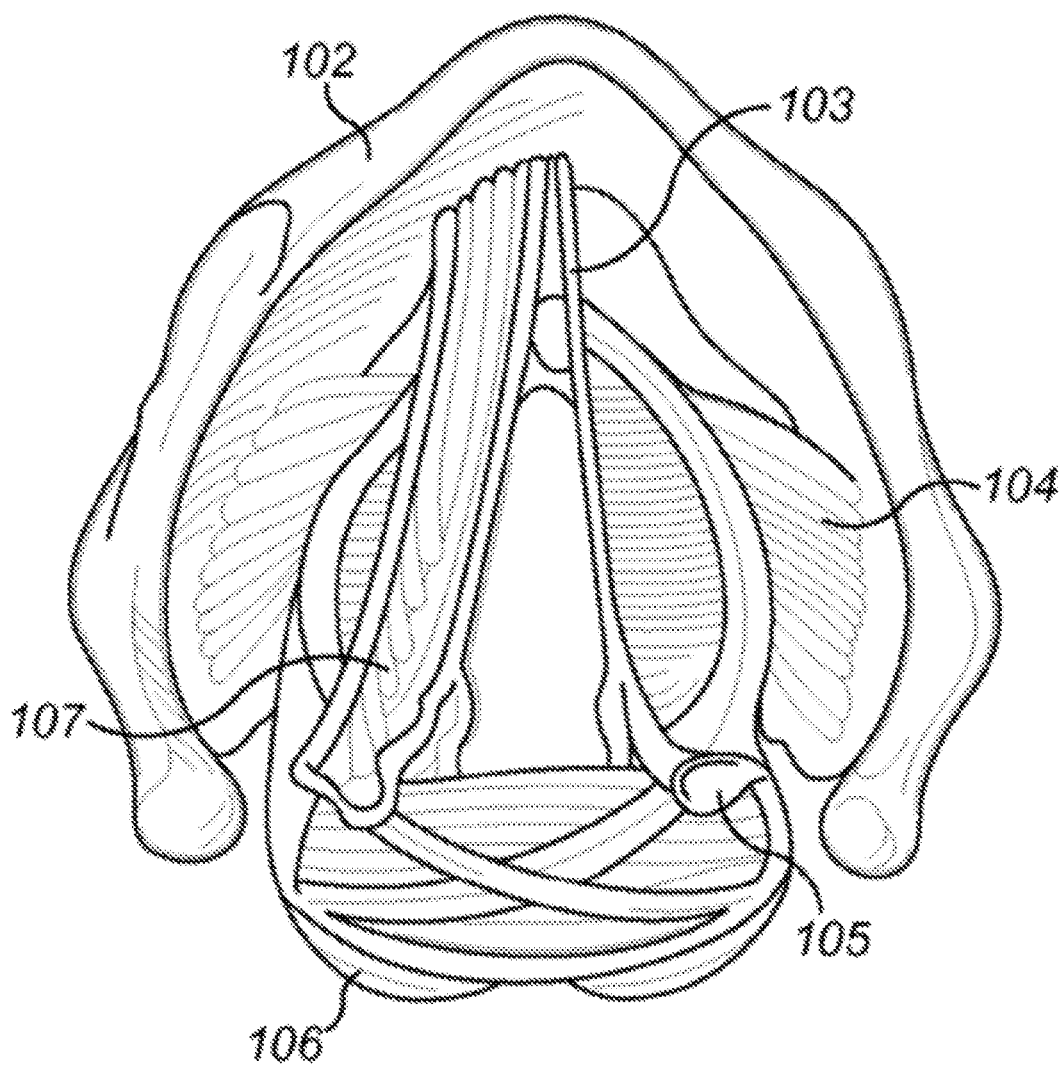
Figure 2:
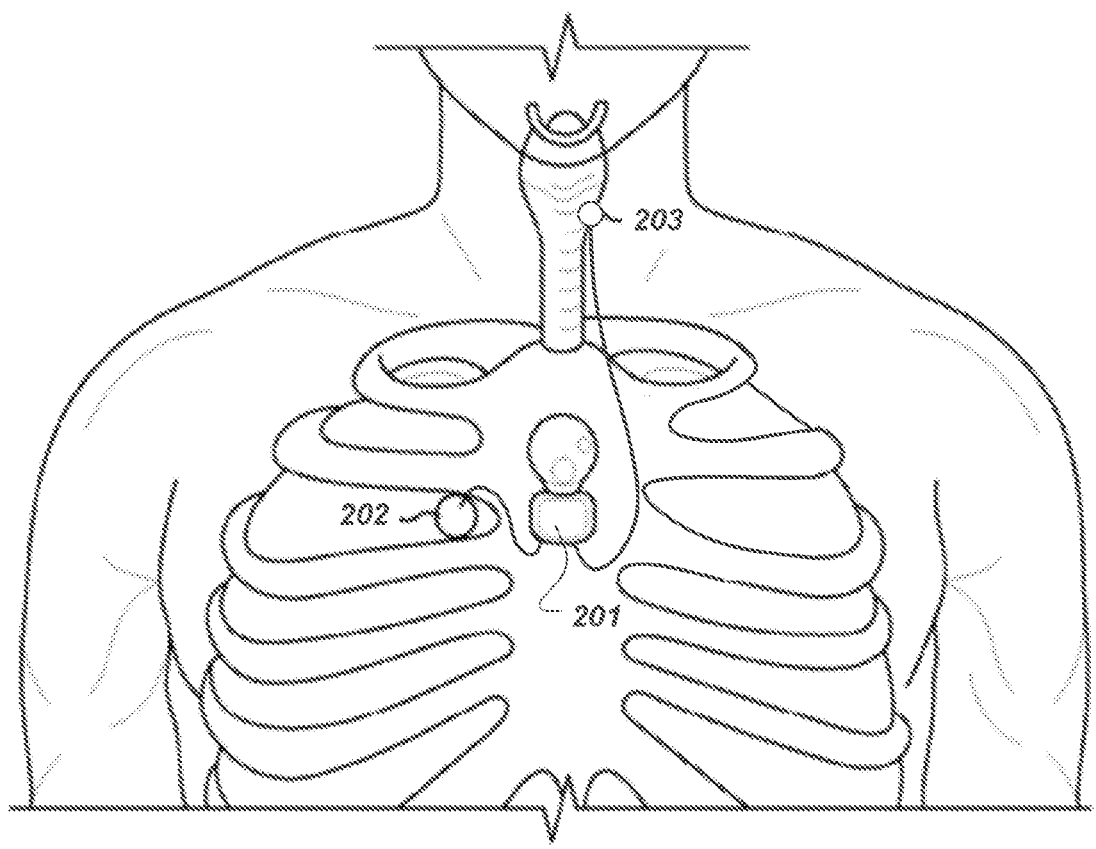
FIG. 2 shows a respiration implant system according to an embodiment of the present invention.

FIG. 2 shows one embodiment of such a respiration implant system with an implanted pacing processor 201 that receives a respiration signal from an implanted respiration sensor 202 implanted in the parasternal muscle that detects respiration activity in the implanted patient. Optionally, a three-axis acceleration movement sensor also is located within the housing of the pacing processor 201 and generates a movement signal. Based on the respiration signal, the pacing processor 201 generates a respiration pacing signal that is synchronized with the detected respiration activity and delivers the pacing signal via a processor lead to a stimulating electrode 203 implanted in the target respiration neural tissue to promote breathing of the implanted patient.

With respect to the specific implementation of a respiration sensor 202, it will be appreciated that during the inspiration phase of breathing, the various respiratory muscles—such as the diaphragm, intercostal externi, and the parasternal part of the intercostal interni muscles (the latter in the following being referred to as the parasternal muscle)—are always active. With every breathing cycle, during inspiration, those muscles are involuntarily active and contract. In particular, the parasternal muscle (also called the intercartilaginous muscle or the parasternal part of the intercostal interni muscle) elevates the ribs during inspiration. Thus, some specific embodiments of the present invention use the contraction of the parasternal muscle, specifically via a parasternal respiration sensor 202 implemented as an electromyogram (EMG) sensor.

The parasternal muscle has a medial to dorsal gradient of activity and muscle mass as well as a cranial caudal gradient, which means that the parasternal muscle becomes smaller from the sternum to the base of the rib. A parasternal respiration sensor 202 can be inserted into or adjacent to the parasternal muscle in a rib interspace in the thorax near the sternum and the pacing processor (see FIG. 2), preferably in the $2^{nd}$ or $3^{rd}$ interspace, and a reliable respiration signal from the parasternal muscle is thereby available. The $2^{nd}$ or $3^{rd}$ interspace provides the thickest proportion of the muscle (around 6-10 mm) in which to secure the respiration sensor 202, and also provides the smallest part of the pectoralis muscle where there is the least overshadowing effect or cross-contamination to be expected. In addition, this location is spatially close to the pacing processor 201 and the surgical placement of the respiration sensor 202 into the parasternal muscle is minimally invasive and surgically uncomplicated.

A parasternal respiration sensor 202 in combination together with a movement sensor/gyroscope also can avoid mis-stimulation during active rotation and bending of the thorax. The parasternal muscle is known to be active during rotation and bending of the thorax, and with the help of the movement sensor these specific bendings and rotations can be measured and mis-stimulation avoided.

Figure 3:
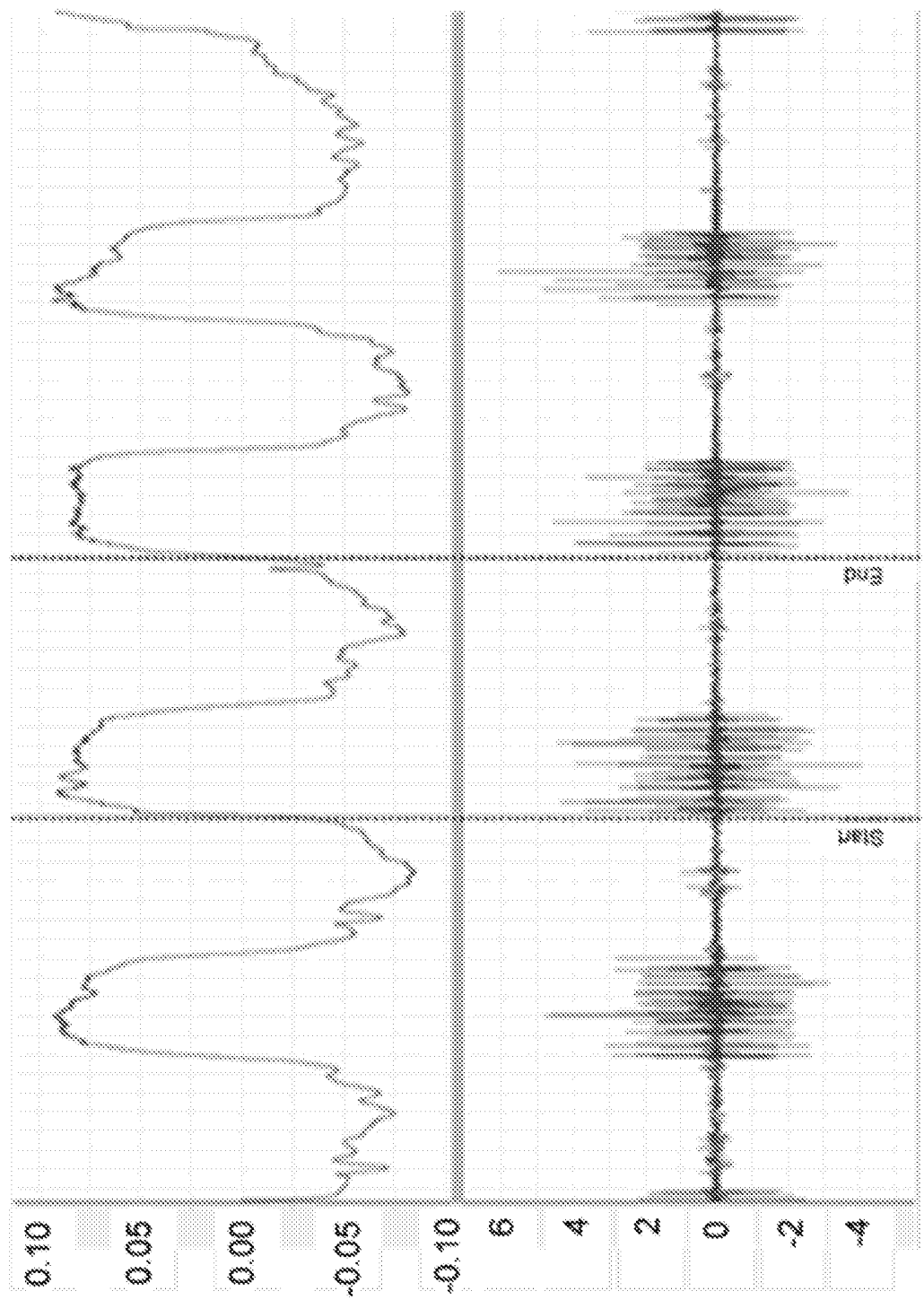
FIG. 3 compares a spirometer reference signal waveform to a parasternal EMG respiration sensor waveform during normal breathing.

The elevation of the ribs by the inspiratory intercostal muscles during inspiration also can be measured via electromyography (EMG) with an intramuscular EMG respiration sensor 202 that senses the electrical activity of the parasternal muscle and detect the onset of inspiration. The placement of a parasternal EMG respiration sensor 202 may be as discussed above for a parasternal pressure sensor, in the parasternal muscle close to the sternum to avoid overshadowing EMG activity of the sensed EMG signal. FIG. 3 compares a spirometer reference signal waveform in the upper portion where positive signals are inspiratory and negative are expiratory, to a parasternal EMG respiration sensor waveform shown in the lower portion. Because the stimulating electrode 206 is placed into the PCA muscle in the larynx relatively distant from the parasternal muscle, no stimulation artifacts will be visible in the parasternal EMG respiration signal.

Figure 4:
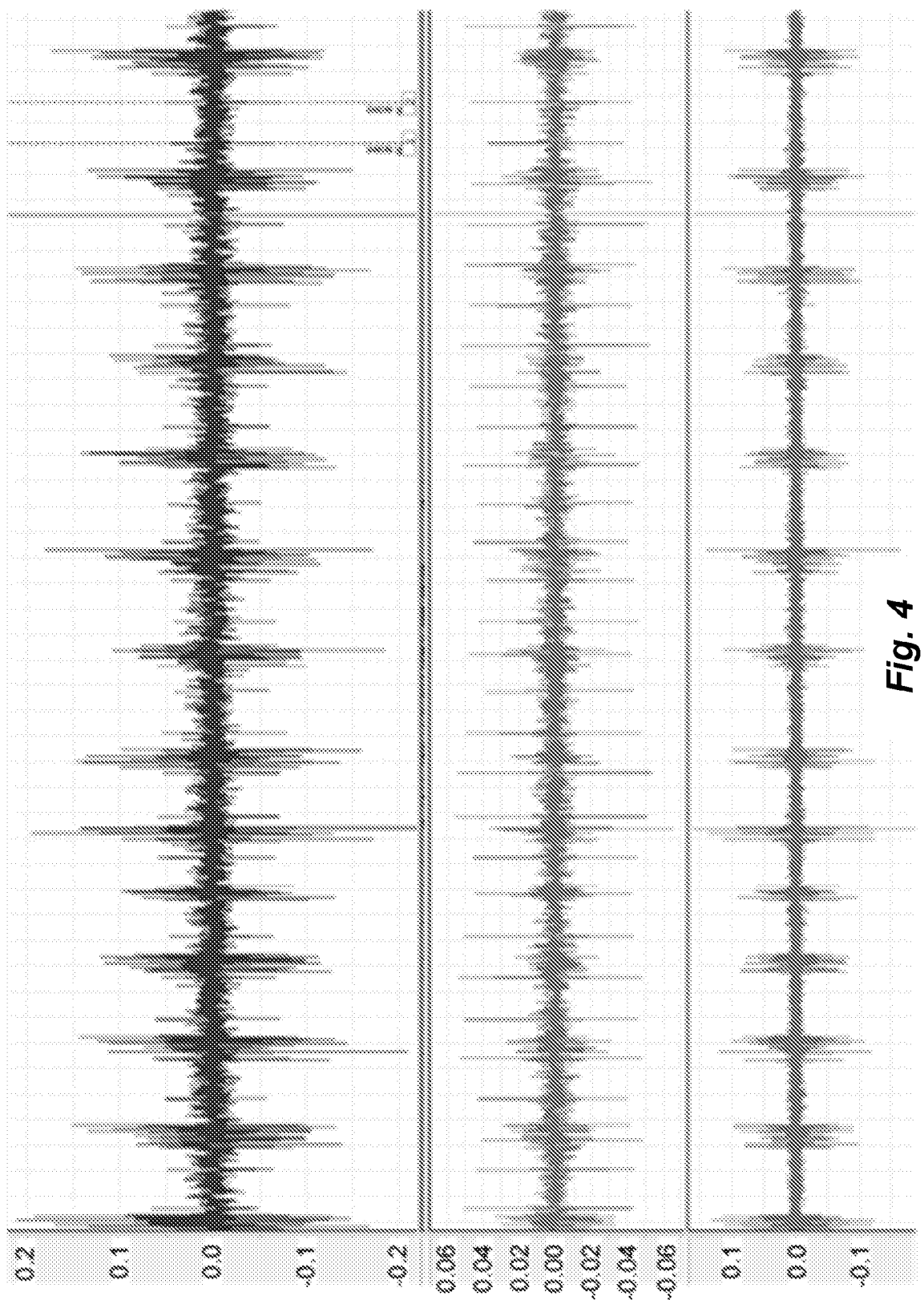
FIG. 4 shows an EMG signal and ECG signal from a recording electrode in the parasternal muscle in a respiration implant system.

An EMG respiration sensor will also detect the largest bio signal in the human body, the electrocardiogram (ECG). Expansion and deflation of the lung during respiration will also move the heart, and the electrical axis of the heart also moves during respiration. This suggests that the EMG and ECG signals might be used together to generate a respiration trigger signal; for example, by detecting the onset of inspiration. In FIG. 4 the top waveform shows the parasternal EMG overlaid with the R-wave peaks of the ECG showing a typical raw waveform as measured by a parasternal EMG sensor. In the middle waveform in FIG. 4, a band pass filter around 10-60 Hz accentuates the ECG R-wave peaks. In the bottom waveform in FIG. 4, a different band pass filter (50-400 Hz) shows extraction of the EMG signal. For each signal, an inspiratory onset can be calculated and the combination of both signals can be used to generate a trigger stimulus for a respiration implant. The addition of the ECG signal extraction can provide a second set of respiratory sensor within the same recording and add value for the detection of the onset of inspiration.

Besides for treatment of impaired laryngeal structures via stimulation of the posterior cricoarytenoid muscle, embodiments of the present invention also may be useful for treatment of sleep apnea. During sleep for those afflicted with this disease, apnea events occur where the airway is blocked (obstructive apneic event) and no air comes in or goes out. The respiratory effort increases (hypopnea) and increases greatly if the airway becomes blocked (apnea). In that situation, all respiratory muscles including the parasternal muscle show increased activation to restart the airflow.

This increased neural activity can be recorded as an increase in respiratory effort in the parasternal muscle sensor, either based on the pressure difference between inspiration and expiration (maximum to minimum pressure) for each breath, or the increased EMG activity can be detected, for example based on the EMG rectified band pass filtered signal between inspiration and expiration. And in such an apnea treatment system, an acceleration-based movement sensor as discussed above can be useful to automatically detect when a person is lying down and sleeping in order to start measuring the respiration signal from the respiration sensor to detect an apnea event. For example, the band pass filtered acceleration signal from the movement sensor (0.1-0.5 Hz) would indicate movement related acceleration from movement of the rib cage.

So if the change in respiratory effort (as determined from the respiration signal and the movement signal) exceeds a certain threshold level and has been increased over recent breaths, then an apnea event is detected. Then the pacing processor can use the respiration signal from the parasternal respiration sensor to determine a given specific point during the respiratory cycle, for example, the start or end of inspiration or expiration. The pacing processor then generates a respiratory-synchronized stimulus signal to the stimulation site (e.g., the hypoglossal nerve or the iSLN) until an improvement is detected in the respiration signal that indicates that the apnea event has been resolved. In some embodiments, triggered respiratory stimulation may commence as soon as the respiratory effort increases slightly in order to prevent the apnea. In other embodiments an untriggered and continuous stimulation may commence as soon as the respiratory effort increases slightly in order to prevent a hypopnea or obstruction during the whole sleep phase.

One problem with locating an EMG within the muscle tissue of the parasternal muscle is that cross contamination of the EMG signal may be caused by sensing electrical activity in other muscles such as the overlying pectoralis muscle. The resulting contaminated signal may not be useable for a respiratory triggered stimulation because no phasic signal will be detectable during activation of the pectoralis muscle (e.g. any arm movements).

Figure 5:
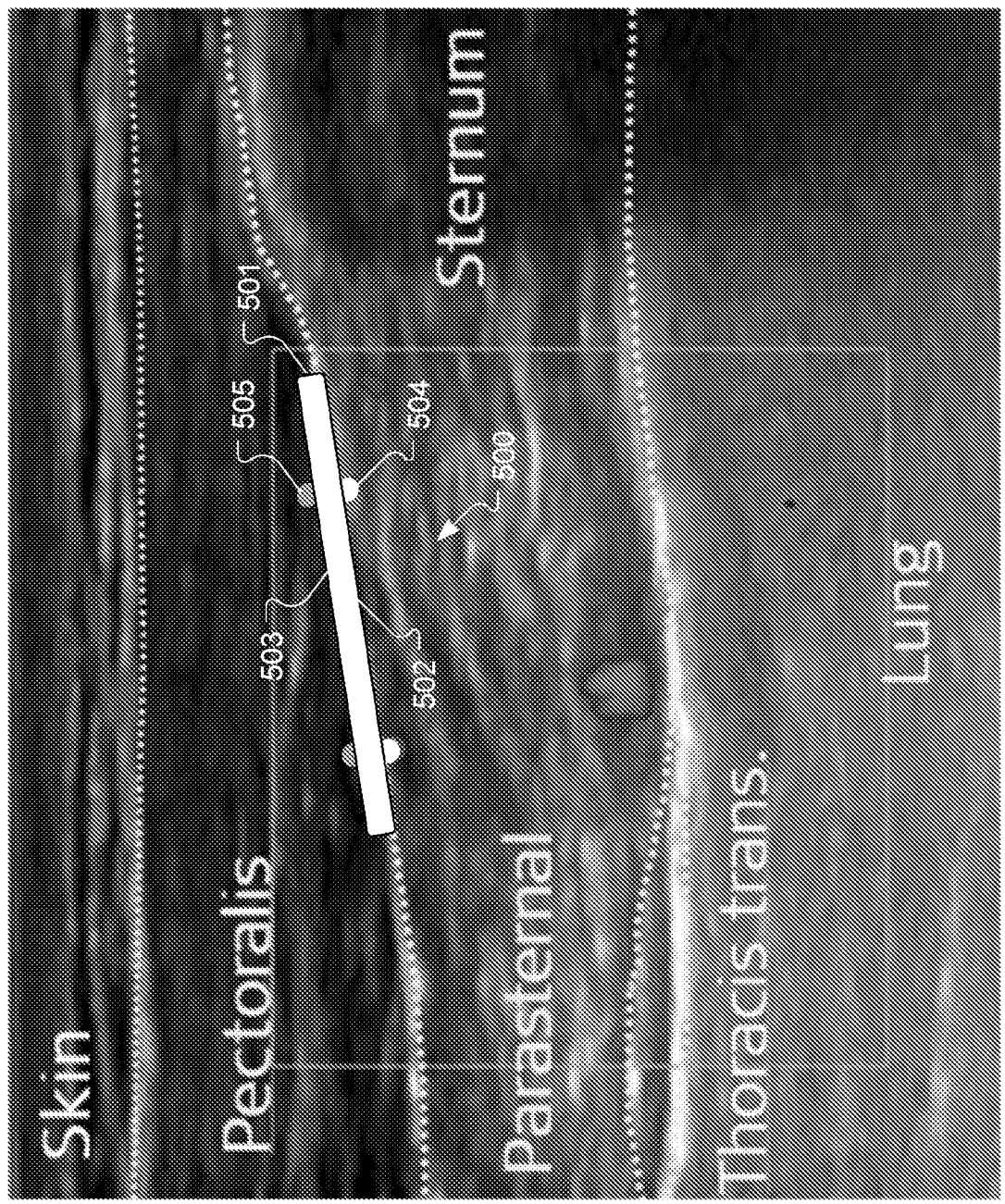
FIG. 5 shows a cross-sectional view of a portion of the respirator muscle structure along with a respiration sensor according to one embodiment of the present invention.

To minimize this cross contamination, embodiments of the present invention include a respiration sensor as shown in FIG. 5, that is configured to be located between the pectoralis muscle and the parasternal muscle rather than inserted into the body of the parasternal muscle as described above. The respiration sensor 500 includes a sensor body 501 that is made of electrically insulating material and that is configured to fit between two adjacent ribs and between the pectoralis muscle and the parasternal muscle of the implanted patient. When implanted within the patient, a bottom surface 502 of the sensor body 501 fits adjacent to an superficial surface of the parasternal muscle, and a top surface 503 of the sensor body 501 fits adjacent to a profound surface of the pectoralis muscle. There is at least one parasternal sensor electrode 504 that is located on the bottom surface 502 of the sensor body 501, which is configured to cooperate with the electrically insulating material of the sensor body 501 to sense a parasternal electromyography (EMG) signal representing electrical activity of the adjacent parasternal muscle with minimal influence by electrical activity of the nearby pectoralis muscle.

The respiration sensor 500 also may include one or more suture attachment points (not shown for clarity) that are attached to the sensor body 501 and configured for fixedly attaching the sensor body 501 to adjacent tissues when the respiration sensor 500 is implanted in the implanted patient so as to prevent migration/rotation over time of the respiration sensor 500.

The specific embodiment of the respiration sensor 500 shown in FIG. 5 further includes at least one pectoralis sensor electrode 505 that is located on the top surface 503 of the electrode body 501 opposite the at least one parasternal sensor electrode 504. The at least one pectoralis sensor electrode 505 is configured to cooperate with the electrically insulating material of the sensor body 501 to sense a pectoralis EMG signal representing electrical activity of the adjacent pectoralis muscle at the same time as the detection of the parasternal EMG signal with the least one parasternal sensor electrode 504 on the bottom surface 502 of the sensor body 501. The pectoralis EMG signal represents an artifact with respect to the parasternal EMG signal, which can be subtracted out by the signal processing algorithm. The resulting processed parasternal EMG signal is then free of the usually much larger pectoralis EMG signal artifact and thus shows more accurately reflects the respiration cycle of the implanted patient. In other embodiments, two different spatially separated sensor paddles may be used, one for recording the parasternal EMG signal, and the other for recording the pectoralis EMG signal. However, having both sensor electrodes combined on a single sensor body reduces the number of implantable components, eases handling for the surgeon, and reduces the surgical trauma of implantation.

The form of the respiration sensor 501 may be similar to paddle electrodes which are used in spinal cord stimulation, i.e., with paddle shaped sensor body 501 that fits in between two adjacent ribs and which should be as short as needed. The width and length of the whole respiration sensor 501 should be as small as possible for minimally invasive surgery, but large enough to suppress the cross contamination signal from the pectoralis muscle.

Figure 6A:
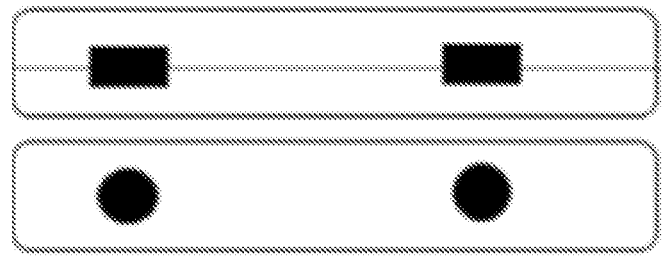
FIG. 6A shows top/bottom plan views of a respiration sensor as in FIG. 5 illustrating various shapes of the sensor electrodes.
Figure 6B:
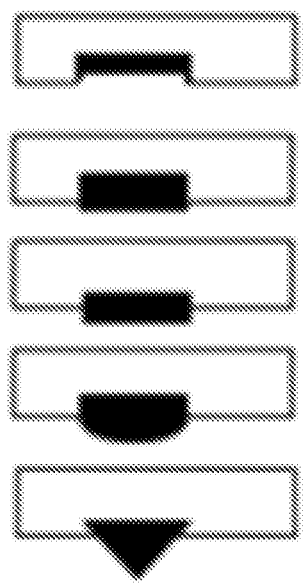
FIG. 6B shows side views of a respiration sensor as in FIG. 5 illustrating various sensor electrode configurations.

The sensor electrode 504/505 may more specifically be a pair of bipolar sensing electrodes as shown in FIG. 5, which may be any useful shape such as round, square or rectangular as shown in FIG. 6A. FIG. 6B shows side views of a respiration sensor as in FIG. 5 with various sensor electrode configurations illustrating that the sensor electrode 504/505 may be recessed below the surface of the sensor body 501, flush with the surface of the senor body 501, or protrude above the surface of the sensor body 501.

In addition to a sensor electrode that detects the two EMG signals as just described, some embodiments also may include an acceleration sensor as previously discussed to detect a patient's movement state. For example, an acceleration sensor may be a component of the processor/stimulator housing. In such an embodiment, power management considerations suggest that it may not be necessary to continuously sense and record both EMG signals and the acceleration signal at all times. In some situations, the parasternal EMG signal alone may be sufficient to reliably detect the respiration cycle; for example, when the patient in at rest with little or no movement. For lowest energy consumption, the pectoralis sensor and the acceleration sensor may then be off.

In general, a power management system may be applied such as disclosed, for example, in U.S. patent application Ser. No. 14/677,018 (which is incorporated herein by reference in its entirety). The acceleration sensor signal can be used to determine whether there is movement or not. As circumstances change—e.g., the patient becomes more active—the pectoralis EMG sensor may be activated to sense the pectoralis EMG signal to be subtracted from the parasternal EMG signal. For example, the implant processor may remove the pectoralis EMG signal from the parasternal EMG signal by a variety of different processing algorithms such as root mean square (RMS) subtraction, Raw Signal subtraction, Teager Kaiser energy subtraction, rectified and band pass filtered subtraction or subtraction with a patient specific weighting factor (determined during a patient fitting session) of any of these different processing algorithms. As circumstance change further—e.g., patient activity increases further—the acceleration sensor may be activated to sense the acceleration signal. These different signal sensing modes may be automatically controlled by the system and/or manually controllable by the patient.

For treatment of sleep apnea, the processed parasternal EMG signal can be used in at least two ways. The difference within one breath between the maximum and minimum value of the rectified and band pass filtered EMG signal can be defined as respiratory effort, which can be calculated from the processed parasternal EMG as described above. Since sleep apnea events occur where the airway is at least partially blocked, the respiratory effort involuntarily increases if the airway starts to narrow, and greatly increases if the airway is entirely blocked. In that situation, all respiratory muscles will exhibit increased innervation in order to re-start the airflow. This increased neural activity will be detected as a respiratory effort increase including in the activity of the parasternal muscle. If the respiratory effort change exceeds a certain threshold and has been increased over the last few respiration cycles, then an apnea event is detected, which triggers a system response. For example, the processed parasternal EMG signal can be further used to detect a specific moment during the respiratory cycle such as the start or end of inspiration or expiration. At that time, the processor can provide triggered treatment signals to implanted stimulation electrodes until the processed parasternal EMG signal improves (indicating that the apnea event is resolved). Alternatively, once an apnea event is detected, a continuous stimulation may automatically commence until the system detects an improvement. Some apnea treatment systems may be configured to start triggered stimulation as soon as here is a slight increase in respiratory effort, so as to avoid a serious apneic event.

For the treatment of sleep apnea, an acceleration sensor as described above can also be used to detect automatically a person's movement state. When the system measures that a person is lying and sleeping, it may commence monitoring the parasternal EMG signal to detect the start of any apneic events. The bandpass filtered acceleration sensor signal (0.1-0.5 Hz) indicates rib cage movement. The acceleration signal together with processed parasternal EMG signal can be used to calculate respiration effort and thereby detect apneic events.

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A respiration implant system for a patient with impaired breathing, the respiration implant system comprising:
    a respiration sensor including:
        a sensor body made of electrically insulating material and having top and bottom surfaces, wherein the sensor body is configured to fit between two adjacent ribs and between the pectoralis muscle and the parasternal muscle of the patient, with the bottom surface adjacent to a superficial surface of the parasternal muscle and the top surface adjacent to a profound surface of the pectoralis muscle;
        at least one parasternal sensor electrode located on the bottom surface of the sensor body and configured to cooperate with the electrically insulating material of the sensor body to sense a parasternal electromyography (EMG) signal representing electrical activity of the adjacent parasternal muscle; and at least one pectoralis sensor electrode located on the top surface of the sensor body opposite the at least one parasternal sensor electrode and configured to cooperate with the electrically insulating material of the sensor body to sense a pectoralis EMG signal representing electrical activity of the adjacent pectoralis muscle; and a pacing processor configured to receive a respiration signal from the respiration sensor, the respiration signal including the parasternal EMG signal and the pectoralis EMG signal, the pacing processor configured to filter out, at least in part, the pectoralis EMG signal from the parasternal EMG signal to generate a respiration pacing signal to be delivered to a stimulation electrode.

2. The respiration implant system according to claim 1, wherein the sensor body is paddle shaped.

3. The respiration implant system according to claim 1, wherein the at least one parasternal sensor electrode comprises a pair of bipolar sensing electrodes.

4. The respiration implant system according to claim 1, wherein the at least one parasternal sensor electrode is round.

5. The respiration implant system according to claim 1, wherein the at least one parasternal sensor electrode is square or rectangular.

6. The respiration implant system according to claim 1, wherein the respiration sensor further comprises:

one or more suture attachment points attached to the sensor body and configured to fixedly attach the sensor body to adjacent tissues when the respiration sensor is implanted in the patient.

7. The respiration implant system according to claim 1, further comprising:

an acceleration movement sensor configured to detect movement of the patient and develop a corresponding movement signal.

8. The respiration implant system according to claim 7, wherein the acceleration movement sensor is located in a housing configured to hold the pacing processor.

9. The respiration implant system according to claim 1, wherein the pacing processor is configured to filter out the pectoralis EMG signal from the parasternal EMG signal using root mean square subtraction, Raw Signal subtraction, Teager Kaiser energy subtraction, rectified and band pass filtered subtraction, subtraction with a patient specific weighting factor or combinations thereof.

10. The respiration implant system according to claim 1, wherein the respiration implant system includes a laryngeal pacemaker system having the stimulation electrode configured to deliver the respiration pacing signal to a posterior cricoarytenoid muscle in the larynx.

11. The respiration implant system according to claim 1, wherein the respiration implant system includes a sleep apnea treatment system having the stimulation electrode configured to deliver the respiration pacing signal to a hypoglossal nerve or an internal superior laryngeal nerve.

* * * * *